United States Patent
Giese et al.

(10) Patent No.: US 10,060,883 B2
(45) Date of Patent: Aug. 28, 2018

(54) PIPELINE CRACK DETECTION

(71) Applicant: General Electric Company, Schenectady, NY (US)

(72) Inventors: Jochen Uwe Giese, Karlsruhe (DE); Andrew Robinson, Sunderland (GB); Markus Holger Blust, Stutensee (DE); Christian Alexander Goldmann, Karlsruhe (DE)

( * ) Notice: Subject to any disclaimer, the term of this patent is extended or adjusted under 35 U.S.C. 154(b) by 243 days.

(21) Appl. No.: 14/873,140

(22) Filed: Oct. 1, 2015

(65) Prior Publication Data
US 2017/0097322 A1 Apr. 6, 2017

(51) Int. Cl.
| | |
|---|---|
| *G01N 29/265* | (2006.01) |
| *G01N 29/04* | (2006.01) |
| *G01N 29/11* | (2006.01) |
| *G01N 29/07* | (2006.01) |
| *G01N 29/06* | (2006.01) |

(52) U.S. Cl.
CPC ........ *G01N 29/07* (2013.01); *G01N 29/0609* (2013.01); *G01N 29/069* (2013.01); *G01N 29/0645* (2013.01); *G01N 29/11* (2013.01); *G01N 29/265* (2013.01); *G01N 2291/044* (2013.01); *G01N 2291/2634* (2013.01)

(58) Field of Classification Search
CPC .. G01N 29/07; G01N 29/0609; G01N 29/069; G01N 29/11; G01N 29/46; G01N 29/0645; G01N 29/265
See application file for complete search history.

(56) References Cited

U.S. PATENT DOCUMENTS

| | | | | | |
|---|---|---|---|---|---|
| 2,795,133 | A | * | 6/1957 | Ots ..................... | G01N 29/28 73/600 |
| 4,147,065 | A | * | 4/1979 | Lather ................. | G01N 29/07 73/611 |
| 4,428,235 | A | * | 1/1984 | Sugiyama ............. | G01N 29/12 73/574 |
| 4,658,649 | A | * | 4/1987 | Brook ................ | G01N 29/0618 73/598 |

(Continued)

FOREIGN PATENT DOCUMENTS

| | | |
|---|---|---|
| CA | 1169541 A1 | 6/1984 |
| JP | 3281878 * | 5/2002 |

(Continued)

OTHER PUBLICATIONS

CyberLogic; "Ultrasound detecting a crack in an oil pipeline using computer simulation;" Retrieved from the internet at http://www.cyberlogic.org/pipeline.html; 2015.

(Continued)

*Primary Examiner* — Helen Kwok
(74) *Attorney, Agent, or Firm* — Mintz Levin Cohn Ferris Glovsky and Popeo, P.C.

(57) ABSTRACT

A method includes emitting an ultrasonic signal into a test specimen from a transducer, receiving a first reflected ultrasonic signal from the test specimen, wherein the first reflected ultrasonic signal is reflected from a feature in the test specimen and the first reflected ultrasonic signal is internally reflected within the test specimen three times prior to being received, and determining a threshold depth of the feature in the test specimen based on receiving the first reflected ultrasonic signal.

20 Claims, 7 Drawing Sheets

(56) References Cited

U.S. PATENT DOCUMENTS

| | | | | |
|---|---|---|---|---|
| 4,698,793 | A * | 10/1987 | Wu | G01V 1/48 367/28 |
| 4,893,286 | A * | 1/1990 | Cobb | E21B 47/082 181/105 |
| 4,953,147 | A * | 8/1990 | Cobb | E21B 47/082 181/105 |
| 5,060,518 | A * | 10/1991 | Aleshin | G01N 29/07 73/620 |
| 5,062,300 | A * | 11/1991 | Vallee | G01N 29/221 73/623 |
| 5,111,696 | A * | 5/1992 | Lund | G01N 29/0609 702/39 |
| 5,492,012 | A * | 2/1996 | Terhune | G01N 29/069 73/596 |
| 5,717,169 | A * | 2/1998 | Liang | E21B 47/00 181/104 |
| 6,014,609 | A * | 1/2000 | McCoy | G01V 1/40 702/6 |
| 6,571,634 | B1 | 6/2003 | Bazarov et al. | |
| 6,578,422 | B2 | 6/2003 | Lam et al. | |
| 6,745,136 | B2 | 6/2004 | Lam et al. | |
| 6,848,313 | B2 | 2/2005 | Krieg et al. | |
| 7,240,554 | B2 | 7/2007 | Berke | |
| 7,299,697 | B2 * | 11/2007 | Siddu | G01N 29/0645 73/587 |
| 7,694,566 | B2 * | 4/2010 | Kleinert | G01N 29/0609 73/598 |
| 7,900,516 | B2 * | 3/2011 | Fukutomi | G01N 29/069 73/598 |
| 7,997,139 | B2 | 8/2011 | Owens et al. | |
| 8,042,399 | B2 | 10/2011 | Pasquali et al. | |
| 8,776,558 | B2 | 7/2014 | Volker | |
| 2006/0230831 | A1 * | 10/2006 | Berke | G01N 29/0645 73/602 |
| 2007/0000328 | A1 * | 1/2007 | Buttram | G01H 5/00 73/597 |
| 2009/0139333 | A1 * | 6/2009 | Hirose | G01N 29/069 73/579 |
| 2011/0296923 | A1 * | 12/2011 | Cataldo | G01N 29/043 73/632 |
| 2016/0025684 | A1 * | 1/2016 | Deneuville | G01N 29/225 73/622 |

FOREIGN PATENT DOCUMENTS

| | | |
|---|---|---|
| WO | 1981002636 A1 | 9/1981 |
| WO | 2004097397 A1 | 11/2004 |

OTHER PUBLICATIONS

Vogel et al; "Ultrasound tool can combine metal loss and crack inspection of gas pipelines;" Pipeline & Gas Journal 234.8; Aug. 2007.

* cited by examiner

PIPELINE CRACK DETECTION

BACKGROUND

A pipeline "pig" is a tool directed through a section of pipeline, typically advanced through the pipeline by the pressure of fluid flow through the pipeline, or other differences in pressure within the pipeline. Pigs may be used to inspect the pipeline with various sensors, to separate fluid flows within the pipeline, to clean the interior surface of the pipeline, to record geometric information about the pipeline, as well as for other purposes. One way to inspect the pipeline is to pass a sensor-carrying pig module (e.g., sensor carrier module) through the pipeline. Transducers mounted to the pipeline pig may be configured to emit ultrasonic signals into the pipeline wall and receive reflected ultrasonic signals, which may be analyzed or processed to detect features (e.g., cracks) in the pipeline. As such, it would be beneficial to use the pipeline pig mounted ultrasonic transducers to identify characteristics of the detected features.

BRIEF DESCRIPTION

Several embodiments of the disclosed subject matter are summarized below. These embodiments are not intended to limit the scope of the disclosed subject matter, but rather these embodiments are intended only to provide a brief summary of possible forms of the disclosed subject matter. Indeed, the disclosed subject matter may encompass a variety of forms that may be similar to or different from the embodiments set forth below.

In a first embodiment, a method includes emitting an ultrasonic signal into a test specimen from a transducer, receiving a first reflected ultrasonic signal from the test specimen, wherein the first reflected ultrasonic signal is reflected from a feature in the test specimen and the first reflected ultrasonic signal is internally reflected within the test specimen three times prior to being received, and determining a threshold depth of the feature in the test specimen based on receiving the first reflected ultrasonic signal.

In a second embodiment, a non-transitory computer readable medium includes executable instructions that when executed cause a processor to determine a threshold depth of a feature in a test specimen based upon a first reflected ultrasonic signal received from the test specimen, wherein the first reflected signal was reflected from the feature and internally reflected within the test specimen three times prior to being received.

In a third embodiment, an ultrasonic pipeline inspection data analysis system includes a processor, communication circuitry, and a display. The ultrasonic pipeline inspection data analysis system is configured to receive pipeline inspection data and determine a threshold depth of a feature in a test specimen based upon a first reflected ultrasonic signal received from the test specimen, wherein the first reflected signal was reflected from the feature and internally reflected within the test specimen three times prior to being received.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

One or more specific embodiments of the disclosed subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

The subject matter disclosed herein relates to inspecting fluid pipelines, and more specifically, to using ultrasonic transducers to identify characteristics (e.g., depth) of detected features (e.g., cracks).

A pipeline may be inspected by passing a pipeline pig with a sensor carrier module through the pipeline. The sensor carrier may be equipped with ultrasonic transducers, piezo ultrasonic transducers, piezocomposite ultrasonic transducers, electromagnetic acoustic transducers (EMATs), magnetic flux sensors, etc. which may be mounted to skids that slide along the interior surface of the pipeline. The sensors may be used to detect the presence of cracks, corrosion, or other features, measure wall-thickness, or otherwise determine the condition of the pipeline.

For example, a transducer may emit an ultrasonic signal and receive reflected ultrasonic signals that have been reflected by the pipeline wall. Echoes in the reflected ultrasonic signals may be indicative of a crack or other features in the pipeline wall. Using the techniques described herein, analysis of the reflected ultrasonic signals collected by the transducer may be used to determine the presence of a feature in the pipeline, as well as one or more characteristics (e.g., depth) of the feature.

Figure 1:
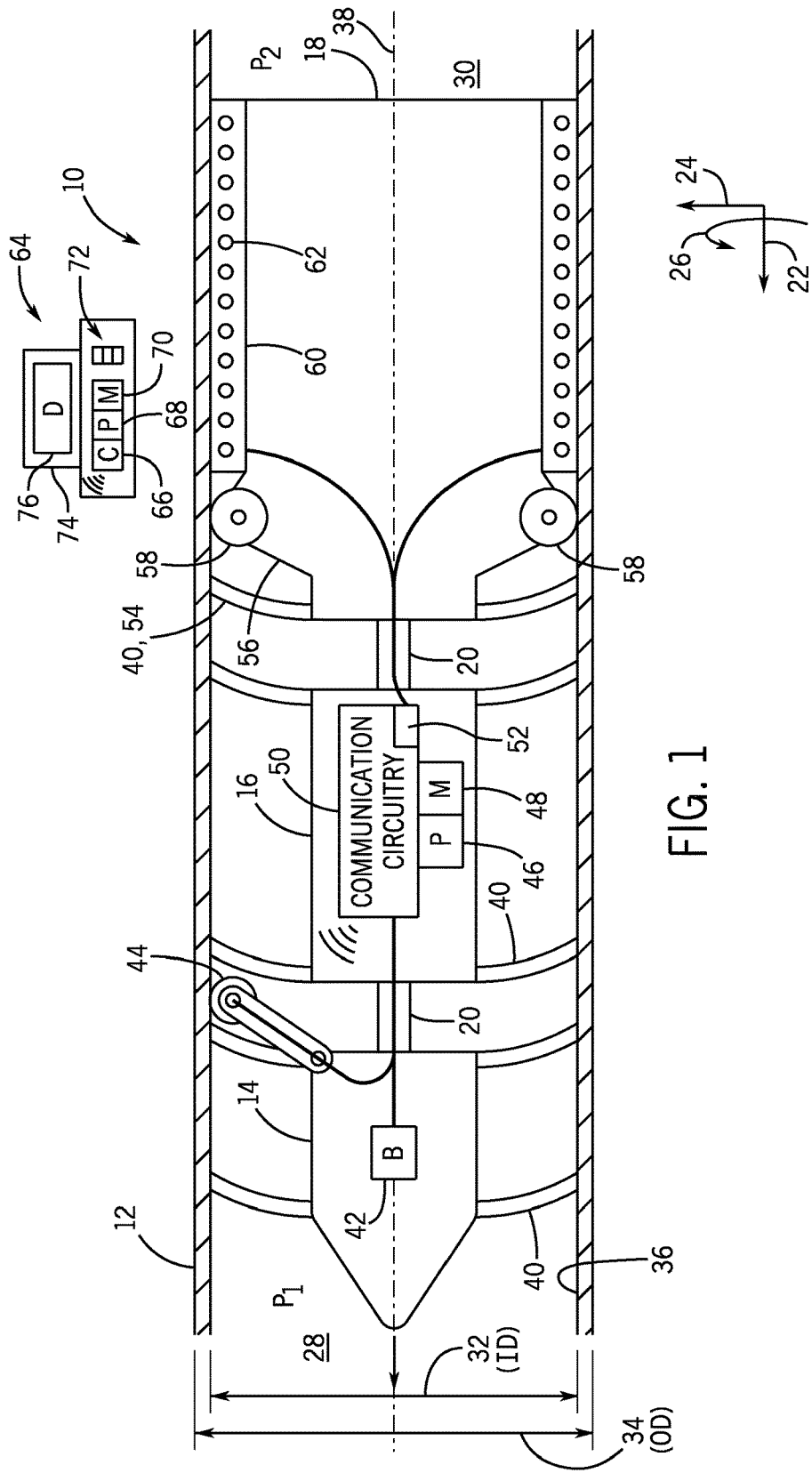
FIG. 1 is a cross-sectional schematic of an embodiment of an exemplary pipeline pig with a sensor carrier module inside a pipeline.

Turning now to the figures, FIG. 1 is a cross-sectional schematic of an exemplary embodiment of a pipeline pig 10 inside a pipeline 12, having a tow (or battery) module 14, a circuitry module 16, and a sensor carrier module 18, connected by linkages 20. For clarity, an axial direction 22, a radial direction 24, and a circumferential direction 26 are shown in FIG. 1. The pipeline 12 may have a downstream end 28, an upstream end 30, an inside diameter 32, an outside diameter 34, and an interior surface 36 (e.g., cylinder interior surface). The pig 10 may have a pig axis 38, which may be substantially aligned with the axis of the pipeline 12.

Each module 14, 16, 18, may have one or more sealing/support members 40 configured to create a seal between the respective module 14, 16, 18 and the interior surface 36 of the pipeline 12, as well as to provide support for, and center, the module 14, 16, 18 in the pipe. Each of the sealing members 40 may reduce or eliminate fluid flow from one side of the sealing member 40 to the other. In some embodiments, the seals created by sealing members 40 may allow for some fluid flow or some pressure equalization. By sufficiently restricting fluid flow, rather than stopping all fluid flow, the sealing members 40 may achieve their purpose. Each sealing member 40 may be an annular seal structure, which may project or protrude radially outward from the module 14, 16, 18 toward the interior surface 36. The sealing member 40 may include a flat disc-shaped annular seal structure, a first conical seal structure, a curved annular seal structure, or any combination thereof.

In the embodiment shown in FIG. 1, the tow module 14 is the first module in the pig 10. However, the order of modules 14, 16, 18 in the pig 10, and even which modules are included in the pig 10, may vary from embodiment to embodiment. That is, some embodiments of the pig 10 may include a scraping, brushing, cleaning, or attracting (e.g., magnetic) module in addition to a sensor carrier module 18. In some embodiments, the tow module 14 may include a battery 42 used to provide power for any components in the pig 10 such as sensors, processors, memory components, communication circuitry, drive components, pneumatics, hydraulics, etc. In some embodiments, the tow module 14 or the circuitry module 16 may include a measuring wheel 44, configured to measure the distance traveled by the pig 10 in the pipeline 12. In some embodiments, the tow module may include drive components (e.g., motors, pumps, pneumatic components, etc.) to facilitate movement of the pig 10 through the pipeline 12.

The tow module 14 may also include one or more sealing members 40 configured to create a seal between the tow module 14 and the interior surface 36 of the pipeline 12. The sealing members 40 may be made of any flexible material capable of forming a seal with the interior surface 36 of the pipeline 12. Though FIG. 1 shows one sealing member 40 toward the front of the tow module 14, and one sealing member toward the rear of the tow module 14, the tow module 14 may have any number of sealing members 40.

In the embodiment shown in FIG. 1, the circuitry module 16 may follow the tow module 14. As previously discussed, in other embodiments, the order of modules may differ among embodiments. The circuitry module 16 may include a processor 46 for executing programs, processing data collected from sensors, and the like. The circuitry module 16 may also include a memory 48 component (e.g., a non-transitory computer readable medium) in communication with the processor 46 that may be used to store data, programs, processing routines, instructions for the processor 46, sensor parameters, etc. The circuitry module 16 may also include communication circuitry 50 configured to communicate data from sensors to the processor 46 and memory 48. The communication circuitry 50 may also communicate collected data to a user or some device wirelessly (e.g., WiFi, Bluetooth, ANT, near field communication, etc.) or through port 52 (e.g., USB, mini or micro USB, CAN, RS232, RS485, or other method of wired data transmission). Data communication may be in real time (i.e., as data is collected), near real time, or after the pig 10 has passed through a section of the pipeline 12.

As with the tow module 14, the circuitry module 16 may include one or more sealing members 40 configured to create a seal between the circuitry module 16, and the interior surface 36 of the pipeline 12, and to minimize fluid flow from one side of the sealing member 40 to the other. As with the tow module 14, the circuitry module 16 may have 1, 2, 3, 4, 5, 6 or more sealing members 40.

In the embodiment shown in FIG. 1, the sensor carrier module 18 may follow the circuitry module 16. The sensor carrier module 18, as with the tow module 14 and the circuitry module 16, may have one or more sealing members 40 to create a seal between the sensor carrier module 18, and the interior surface 36 of the pipeline 12, and to minimize fluid flow from one side of the sealing member 40 to the other. The sealing member 40 may also be used to provide support for the sensor carrier module 18 and/or center the sensor carrier module 18 in the pipeline 12.

In the embodiment shown in FIG. 1, the leading sealing member 54 of the sensor carrier module 18 may be followed by a generally annular shaped flexible section 56. The flexible section 56 may be a flexible annular structure or assembly which is configured to expand and contract in the radial direction 24. For simplicity, the section may be described as a flexible cone section in the following discussion. The cone section 56 may include a plurality of parts arranged in a conical shape or be made of a single monolithic piece.

A plurality of rotational guides 58 such as rollers, balls, or wheels may be attached to the cone section 56, disposed about the cone section 56 in the circumferential direction 26 such that the rotational guides 58 are in contact with the interior surface 36 of the pipeline 12, or separated from the interior surface 36 of the pipeline 12 by a thin film of fluid. Although the rotational guides 58 may be any rotational structure such as rollers, balls, or wheels, the following discussion refers to the rotational guides 58 as wheels for simplicity. However, it should be understood that the wheels 58 are intended to cover any rotational structure that helps to reduce friction. In some embodiments, the wheels 58 may be of any suitable shape such that they roll along the interior surface 36 of the pipeline 12 as the pig 10 and sensor carrier module 18 move through the pipeline 12. The illustrated embodiments may include any number of wheels 58 (e.g., 1, 2, 3, 4, 5, 6, 7, 8, 9, 10, 11, 12, 13, 14, 15, 20, 30, 40, 50, or more wheels). While this specification discusses rotational guides, other types of non-rotational guides that reduce friction are also possible.

The plurality of wheels 58 may be coupled to and may be followed by a plurality of slat-shaped skids 60 (e.g., axially extending skids), which may be disposed in the circumferential direction 26 such that the skids 60 are in contact with the interior surface 36 of the pipeline 12, or separated from the interior surface 36 of the pipeline 12 by a thin film of fluid (e.g., couplant medium). The skids 60 may include a plurality of sensors 62 disposed in a row or an array down the length of each skid 60.

In some embodiments, the sensors 62 may be recessed from the surface of the skid 60 such that the sensors are spaced within a desired distance from the interior surface 36 of the pipeline. In some embodiments, the sensor 62 may be placed between approximately 0 millimeters and 100 millimeters from the interior surface 36 of the pipeline 12, although larger distances are possible. In other embodiments, the sensor 62 may be placed between approximately 10 millimeters and 50 millimeters from the interior surface 36 of the pipeline 12. In some embodiments, the lower value in the range of acceptable sensor 62 spacing from the interior surface 36 may be 5, 6, 7, 8, 9, 10, 15, 20, 25, 30, 35, 40, 50, 60, 70, 80, 90, or 100 millimeters, or any number in between. Similarly, the higher value in the range of acceptable sensor 62 spacing from the interior surface 36 may be 20, 25, 30, 31, 32, 33, 34, 35, 36, 37, 38, 39, 40, 45, 50, 55, 60, 65, 70, 75, 80, 85, 90, 95, or 100 millimeters, or any number in between.

In general, if the downstream 28 ends of the skids 60 remain in contact, or in near contact with the interior surface 36 of the pipeline, the sensors 62 maintain the desired spacing with the interior surface 36 of the pipeline. The sensors 62 may be any ultrasonic transducers (e.g., piezo ultrasonic transducers, piezocomposite ultrasonic transducers, etc.) configured to detect or size cracks in the pipeline 12, or any other kind of sensor which may be used to inspect a section of pipeline 12.

In the present embodiment shown in FIG. 1, the pig 10 may be propelled through a section of pipeline 12 by a difference between the pressure P1 ahead of the pig 10 and the pressure P2 behind the pig 10, as maintained by, for example, the plurality of sealing members 40. The pig 10 may pass through the section of pipeline 12 based upon the pressure of a fluid flowing through the pipeline 12 or based upon fluid pressure using a pump in an upstream direction 30 or downstream direction 28 of the pig. It should be understood, however, that other techniques for pushing, pulling, propelling, or otherwise passing the pig 10 through the section of pipeline 12 may be used. For example, the pig 10 may be pulled through the pipeline 12 using a cable, or the pig 10 may propel itself (e.g., with driven wheels, a conveyer belt like track, etc.) through the section of pipeline 12 using a motor or some other method.

Data collected using the pipeline pig 10 may be analyzed using a computing device 64 (e.g., computer, tablet, mobile device, etc.). The computing device 64 may include communication circuitry 66, a processor 68, memory 70, communication ports 72, and a user interface 74, which may include a display 76. Following the pipeline pig 10 being passed through a pipeline 12 to take measurements, data may be passed to the computer 64 wirelessly or through a wired connection via communication ports 52, 72. The computer 64 may be located near the pipeline pig 10 or remote from the pipeline pig 10. In some embodiments (e.g., the computer 64 is located remotely relative to the pipeline pig 10), the data may be passed to the computer 64 via the cloud or over a network. In other embodiments, the computer 64 may be in wireless communication with the pipeline pig 10 while the pipeline pig 10 is traveling through the pipeline 12 and analyzing data in real time or near real time. The computer 64 may be outfitted with software stored on the memory component 70 and executed by the processor 68 to facilitate analysis of the collected data. For example, the computing device 64 may be capable of processing the data collected by the sensors (e.g., identifying echoes in the data, determining how the ultrasonic signals were reflected within the pipeline wall), and identify features in the pipeline wall, as well as additional characteristics (e.g., depth) of the identified features.

Though FIG. 1 shows one application of the disclosed techniques, using a pipeline pig 10 to inspect a pipeline 12, this is merely an example and not intended to limit the scope of the disclosed techniques. For example, the disclosed techniques may be used to identify the presence of and characteristics of one or more features in a wall 80, or any other piece of material using ultrasonic transducers.

Figure 2:
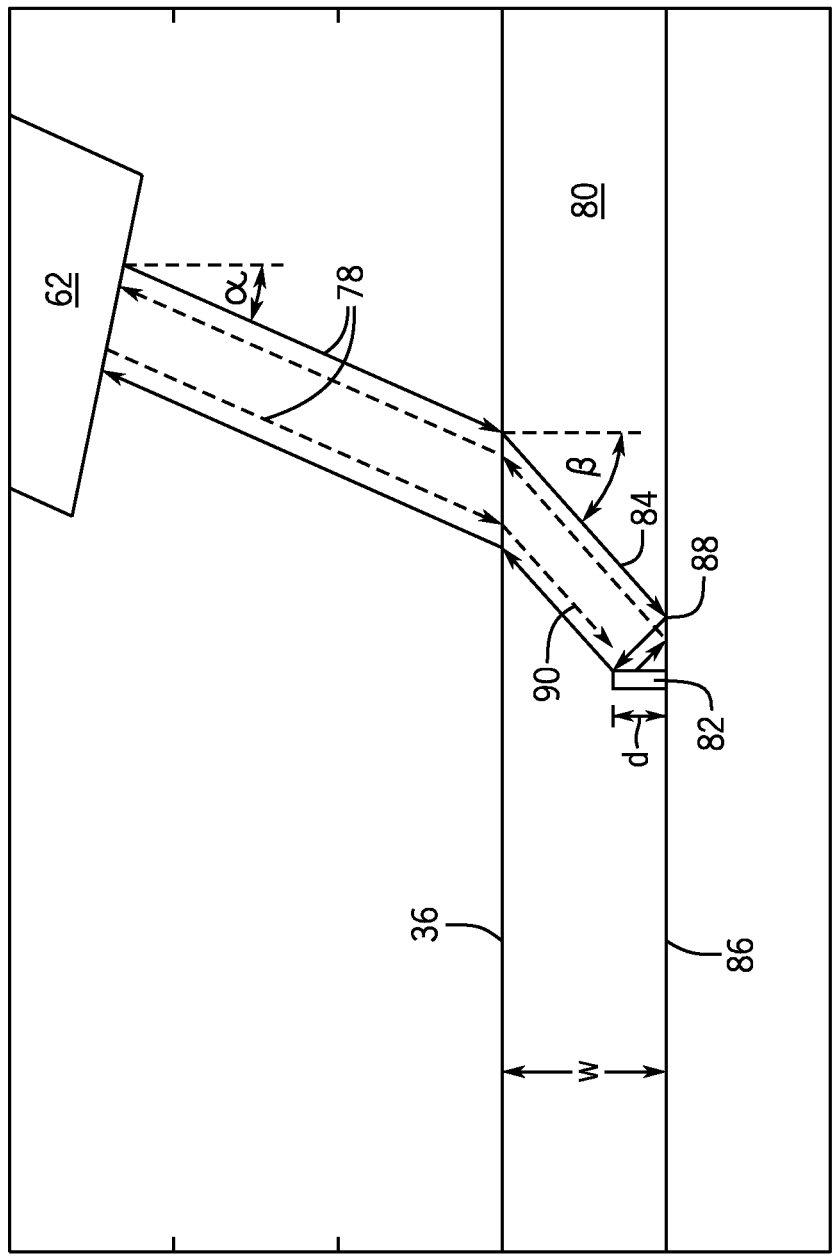
FIG. 2 shows a ray trace of one embodiment of a "half skip" ultrasonic signal echo.
Figure 3:
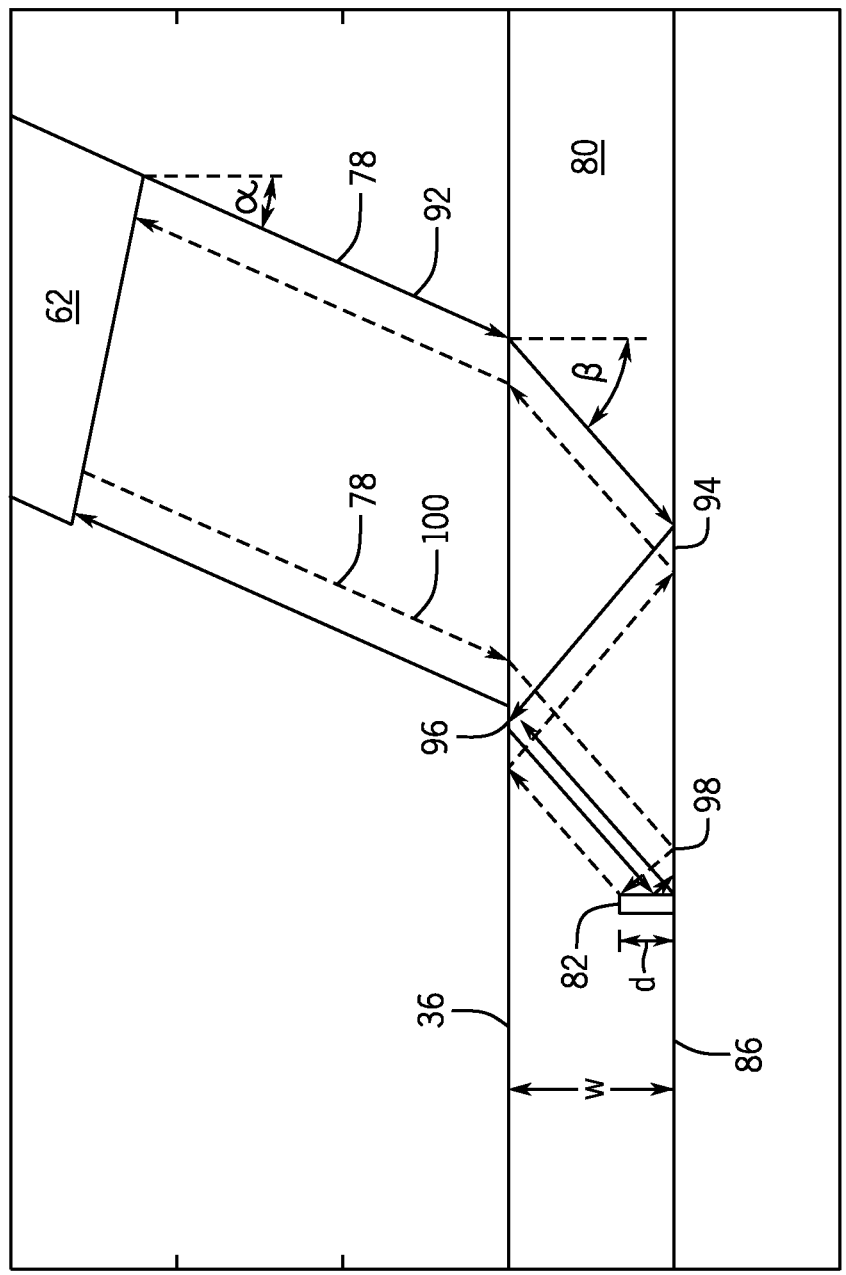
FIG. 3 shows a ray trace of one embodiment of a "one skip" ultrasonic signal echo.
Figure 4:
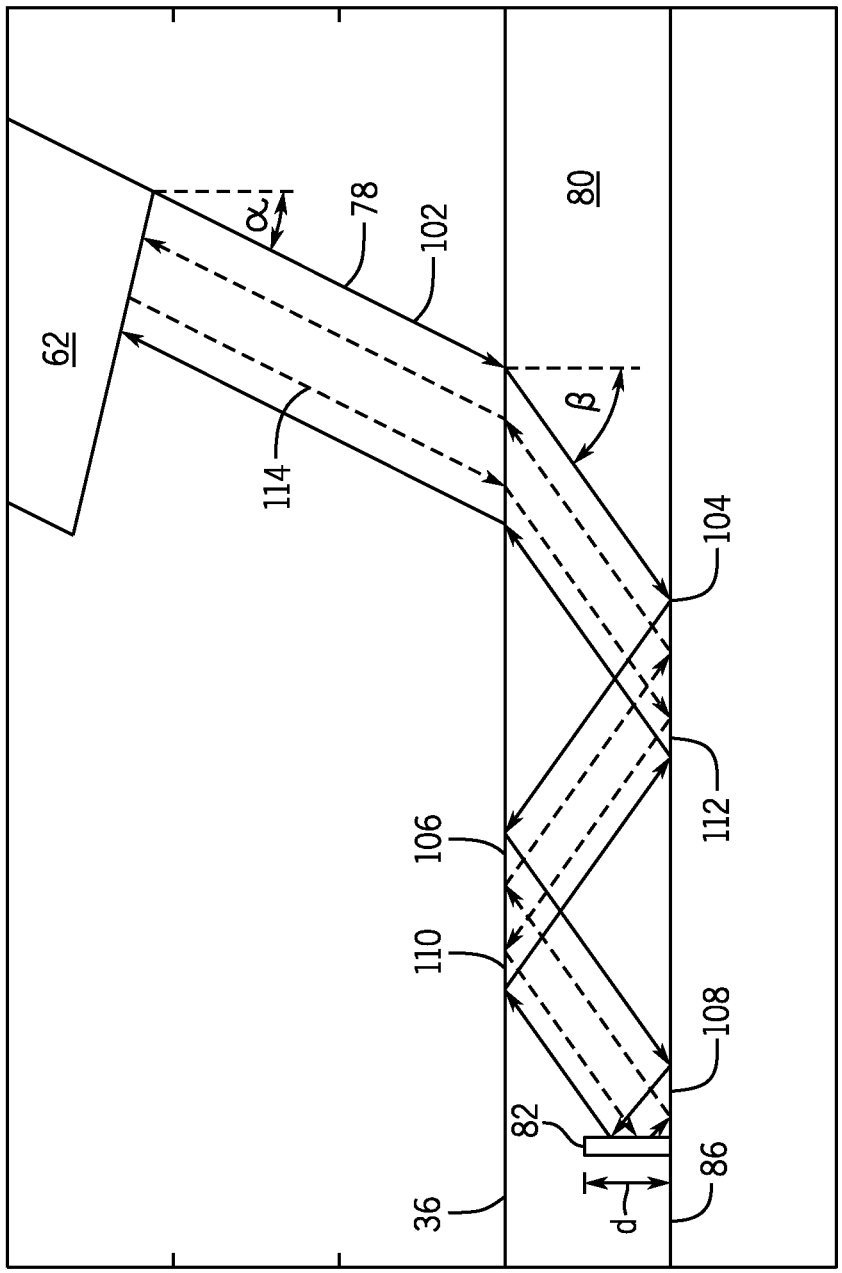
FIG. 4 shows a ray trace of one embodiment of a "one-and-a-half skip" ultrasonic signal echo.

FIGS. 2-4 show ray traces of half-skip, one-skip, and one-and-a-half-skip ultrasonic signal echoes received by the sensor 62 that indicate a feature (e.g., a crack) in a piece of material. FIG. 2 shows a ray trace of a "half-skip" ultrasonic signal echo. In FIG. 2, an ultrasonic transducer 62 emits an ultrasonic signal 78 into a wall 80 of the pipeline 12, the ultrasonic signal 78 reflects off of a feature 82, and back to the ultrasonic transducer. The pipeline wall 80 has a thickness, w, and the feature 82 has a depth, d. The ultrasonic signal 78 is emitted from the transducer 62 and interacts with the interior surface 36 of the pipeline wall 80 at an incidence angle, a. The ultrasonic signal 78 is then refracted and propagates through the pipeline wall 80 at a propagation angle, β. At least a portion of the ultrasonic signal 78 may then follow one of two paths. In the first path 84, the ultrasonic signal 78 reflects off of the exterior surface 86 of the pipeline wall 80 at a location 88, reflects off of the feature 82, toward the interior surface 36 of the pipeline wall 80, then refracts back to the transducer 62. In the second path 90, the ultrasonic signal 78 reflects off of the feature 82, reflects off of the exterior surface 86 of the pipeline wall 80 at location 88, toward to the interior surface 36 of the pipeline wall 80, then refracts back to the transducer 62. These two paths 84, 90, in which the ultrasonic signal is reflected from a feature and internally reflected of the exterior surface 86 are referred to as a half-skip echo, or 0.5 skip echo.

Typically, feature 82 detecting pipeline inspection tools have been designed and set up such that features in the pipeline 12 only return a single indication or echo in order to detect the presence of a feature 82. Multiple echoes have generally been seen as a nuisance and indicative of improperly set up sensors 62. In the presently disclosed techniques, half-skip echoes, as well as additional echoes of the ultrasonic signal 78 (e.g. one-skip echoes and one-and-a-half skip) are collected and analyzed to determine one or more characteristics of the detected feature.

FIG. 3 shows a ray trace of a "one-skip" ultrasonic signal echo. As with FIG. 2, in FIG. 3, the ultrasonic signal 78 is emitted from the transducer 62 and interacts with the interior surface 36 of the pipeline wall 80 and at incidence angle, α. The ultrasonic signal 78 is refracted and propagates through the pipeline wall 80 at a propagation angle, β. At least a portion of the ultrasonic signal 78 may then follow one of two paths. In the first path 92, the ultrasonic signal 78 reflects off of the exterior surface 86 of the pipeline wall 80 at a first location 94, reflects off of the interior surface 36 of the pipeline wall 80 at a second location 96, reflects off of the feature 82, reflects off of the exterior surface 86 of the pipeline wall 80 at a third location 98, toward the interior surface 36 of the pipeline wall 80, then refracts back to the transducer 62. In the second path 100, the ultrasonic signal 78 reflects off of the exterior surface 86 of the pipeline wall 80 at the third location 98, reflects off of the feature 82, reflects off of the interior surface 36 of the pipeline wall 80 at the second location 96, reflects off of the exterior surface 86 of the pipeline wall 80 at the first location 94, toward the interior surface 36 of the pipeline wall, then refracts back to the transducer 62. These paths 92, 100, in which the ultrasonic signal 78 is reflected from the feature and internally reflected within the pipeline wall 80 three times are referred to as a one-skip echo, or 1.0 skip echoes.

FIG. 4 shows a ray trace of a "one-and-a-half skip" ultrasonic signal echo. As with FIGS. 2 and 3, in FIG. 4, the ultrasonic signal 78 is emitted from the transducer 62 and interacts with the interior surface 36 of the pipeline wall 80 and at incidence angle, a. The ultrasonic signal 78 is refracted and propagates through the pipeline wall 80 at a propagation angle, β. The ultrasonic signal 78 may then follow one of two paths. In the first path 102, the ultrasonic signal 78 reflects off of the exterior surface 86 of the pipeline wall 80 at a first location 104, reflects off of the interior surface 36 of the pipeline wall 80 at a second location 106, reflects off of the exterior surface 86 of the pipeline wall 80 at a third location 108, reflects off of the feature 82, reflects off of the interior surface 36 of the pipeline wall 80 at a fourth location 110, reflects off of the exterior surface 86 of the pipeline wall 80 at a fifth location 112, toward the interior surface 36 of the pipeline wall, then refracts back to the transducer 62. In the second path 114, the ultrasonic signal 78 reflects off of the exterior surface 86 of the pipeline wall 80 at the fifth location 112, reflects off of the interior surface 36 of the pipeline wall 80 at the fourth location 110, reflects off of the feature 82, reflects off of the exterior surface 86 of the pipeline wall 80 at the third location 108, reflects off of the interior surface 36 of the pipeline wall 80 at the second location 106, reflects off of the exterior surface 86 of the pipeline wall 80 at the first location 104, toward the interior surface 36 of the pipeline wall 80, then refracts back to the transducer 62. These paths 102, 114, in which the ultrasonic signal is reflected from the feature and internally reflected within the pipeline 12 wall 80 five times are referred to as a one-and-a-half skip echo, or 1.5 skip echoes.

FIGS. 2-4 show features 82 that begin at the exterior surface 86 of the pipeline wall 80 and propagate inward toward the interior surface 36 of the pipeline wall 88. It should be understood, however that this is not intended to be limiting and that the disclosed techniques may be applied to features 82 that begin at the interior surface 36 of the pipeline wall 80 and propagate outward toward the exterior surface 86 of the pipeline wall 86, or features 82 that exist in the middle of the pipeline wall 80 and do not reach either the exterior surface 86 or the interior surface 36 of the pipeline wall 80.

Figure 5:
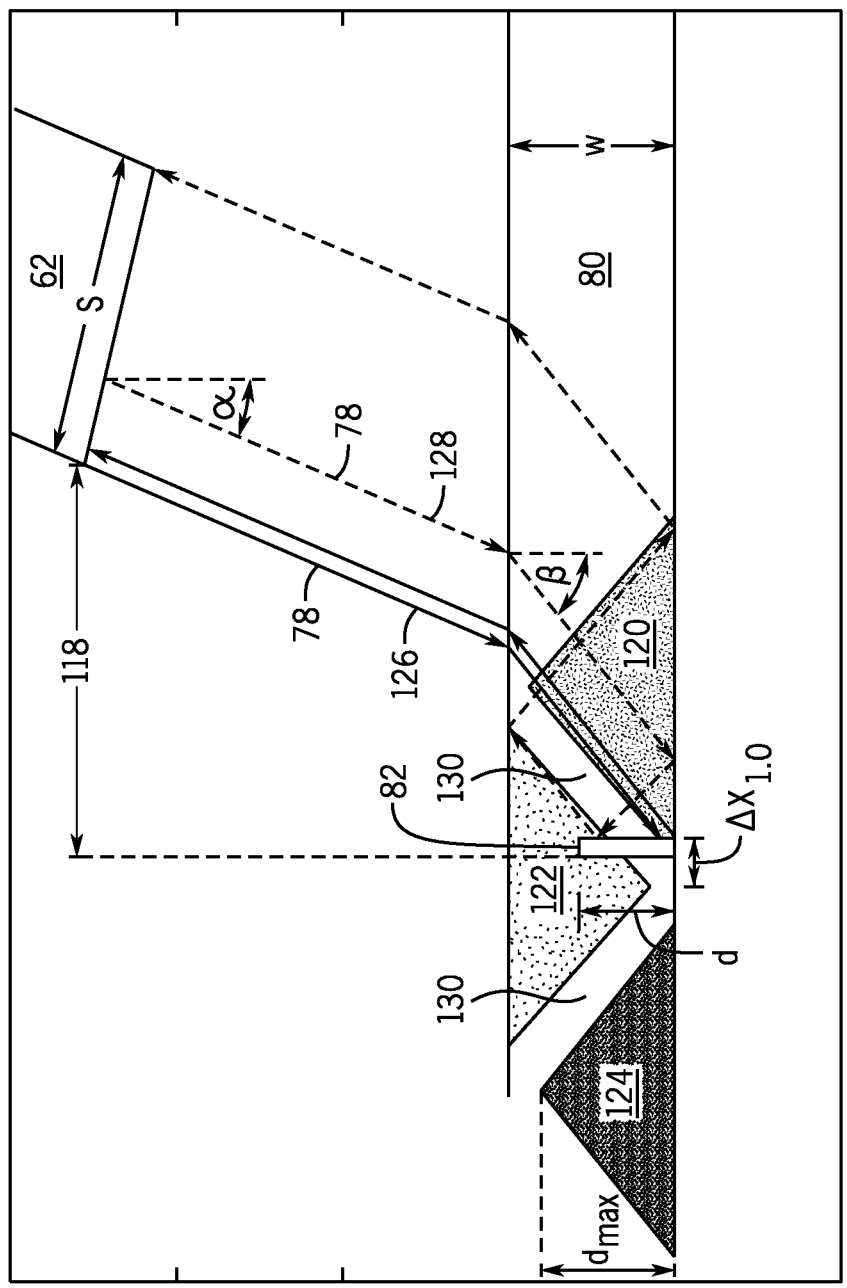
FIG. 5 shows a schematic of one embodiment of half-skip, one-skip, and one-and-a-half-skip coverages areas.

FIG. 5 shows a schematic of one embodiment of half-skip, one-skip, and one-and-a-half-skip coverages areas for the transducer 62 at a known position 118 or distance from feature 82. If the feature 82 is disposed within the half-skip coverage area 120 and propagates in a direction substantially perpendicular to the pipeline wall 80, as shown in FIG. 5, the ultrasonic transducer 62 at position 118 will detect a half-skip echo. Similarly, if the feature is disposed within the one-skip coverage area 122, as shown in FIG. 5, the ultrasonic transducer 62 will detect a one-skip echo. If the feature 82 is disposed within the one-and-a-half skip coverage area 124, the ultrasonic transducer 62 will detect a one-and-a-half skip echo. Note that in FIG. 5, the feature 82 is not within the one-and-a-half skip coverage area 124. As described in more detail below, it is possible, and in some cases even expected, for the transducer 62 to receive multiple echoes. It should be noted that the spaces between coverage areas 120, 122, 124 indicate areas that are not covered by the transducer 62. That is, a feature 82 disposed entirely in space 130 (i.e., the feature 82 does not extend into coverage areas 120, 122, 124) will not be detected by the transducer because no echoes will be returned. However, because the sensor carrier module 18 of a pipeline pig 10 has multiple skids 60 disposed circumferentially 26 about the interior surface 36 of the pipeline, and each skid 60 has multiple sensors 62 disposed axially 22 along the length of the skid, the feature 82 is likely to fall within the coverage areas 120, 122, 124 of the sensor 62 as it travels through the pipeline 12, or a neighboring sensor, or one of the many other sensors. Additionally, it should be understood that the sensors 62 may be arranged in order to minimize coverage gaps. Similarly, in some embodiments signals may be compared between sensors 62 to determine if the sensed echo is a half-skip, a one-skip, or a one-and-a-half skip echo.

The feature 82 may be disposed in more than one coverage area 120, 122, 124. In such cases, the ultrasonic transducer 62 may receive multiple reflected ultrasonic signals indicative of multiple skip echoes. For example, in FIG. 5, the feature 82 is in the half-skip coverage area 120 and the one-skip coverage area 122. Thus, the ultrasonic transducer 62 will return both a half-skip echo and a one skip echo (as indicated by the half-skip ray trace 126 and the one-skip ray trace 128 shown in FIG. 5). Indeed, the various combination of returned signals (e.g., echoes) may be used to determine the threshold depth (e.g., d) or minimum depth of the feature 82 based on which echoes are received (rather than the amplitudes of the received echoes).

As previously discussed, a one-skip echo will appear if the feature 82 propagates from the exterior surface 86 of the pipeline wall 80 and falls within the one-skip coverage area 122. That is, a one-skip echo will appear if:

$$d_{1.0} \geq w - \frac{1}{\tan\beta}\left(\frac{s}{2\cos\alpha} - |\Delta x_{1.0}|\right), \quad (1)$$

Wherein d is the depth of the feature, w is the wall thickness of the pipeline, s is the width of the transducer 62 oscillator, α is the incidence angle of the ultrasonic signal, β is the propagation angle of the ultrasonic signal through the pipeline wall 80, $d_{max}$ is the maximum depth of the coverage areas 120, 122, 124, and $\Delta x_{1.0}$ is the distance of the feature 82 in the axial direction 22 from the center of the one-skip coverage area 122. If the exact position of the feature 82 relative to the sensor 62 (e.g., $\Delta x_{1.0}$) is unknown, then a lower bound of $d_{1.0}$ may be determined by setting $\Delta x_{1.0}$ to zero, such that:

$$d_{1.0} \geq w - \frac{s}{2\tan\beta\cos\alpha}. \quad (2)$$

If a one-skip echo appears with either a half-skip echo, or a one-and-a-half-skip echo simultaneously, then the feature spans across the half-skip coverage area 120 and the one-skip coverage area 122 (as shown in FIG. 5), or the feature 82 spans across the one-skip coverage area 122 and the one-and-a-half-skip coverage area 124. Thus:

$$|\Delta x| \geq w\tan\beta - \frac{s}{2\cos\alpha} \quad (3)$$

and thus, by substituting Equation 3 for Δx in Equation 1 above:

$$d \geq 2w - \frac{s}{\tan\beta\cos\alpha}. \quad (4)$$

Thus, a half-skip echo by itself indicates the presence of the feature 82. A one-skip echo by itself indicates that:

$$d \geq d_{1.0} := w - \frac{s}{2\tan\beta\cos\alpha}. \quad (5)$$

A half-skip echo and a one-skip echo indicates that:

$$d \geq d_{0.5;1.0} := 2w - \frac{s}{\tan\beta\cos\alpha}. \quad (6)$$

A one-skip echo and a one-and-a-half-skip echo indicates that:

$$d \geq d_{1.0;1.5} := 2w - \frac{s}{\tan\beta\cos\alpha}. \quad (7)$$

Accordingly, based upon the presence of half-skip, one-skip, and one-and-a-half-skip echoes in the ultrasonic signal 78 received by the ultrasonic transducer 62, the threshold depth of the detected feature 82 may be determined. Though FIGS. 2-5 show a feature 82 propagating from the exterior surface 86 of the pipeline wall 80, Equations 6-7 hold true for features 82 propagating from the interior surface 36 of the pipeline wall 80. Equation 5 holds true for features 82 propagating from the interior surface 36 of the pipeline wall 80 if either a half-skip echo or a one-and-a-half-skip echo is returned. It should be noted that these techniques allow for the determination of minimum or threshold feature depth based on the existence of echoes, rather than the amplitudes of the echoes. For example, the mere presence of a half-skip echo and a one-skip echo means that a feature is deep enough to span across the half-skip coverage area 120 and the one-skip coverage area 122, or vice versa. Similarly, the presence of a one-skip and a one-and-a-half-skip echo means that a feature is deep enough to span across the one-skip coverage area 122 and the one-and-a-half-skip coverage area 124, or vice versa. A one-skip echo by itself means that a feature propagating from the exterior surface 86 of the pipeline wall 80 is deep enough to propagate into the one-skip coverage area 122. In some embodiments, multiple readings from the transducer 62 as it passes through the pipeline 12, or readings from neighboring transducers 62 may be combined and/or compared to determine more about the feature 82 (e.g., position, a more detailed depth determination, etc.). Accordingly, by relying on the mere presence of an echo rather than the amplitude of the echo, data processing and set up (e.g., setting a threshold amplitude) is simplified and does not require evaluation of the echo amplitude.

Figure 6:
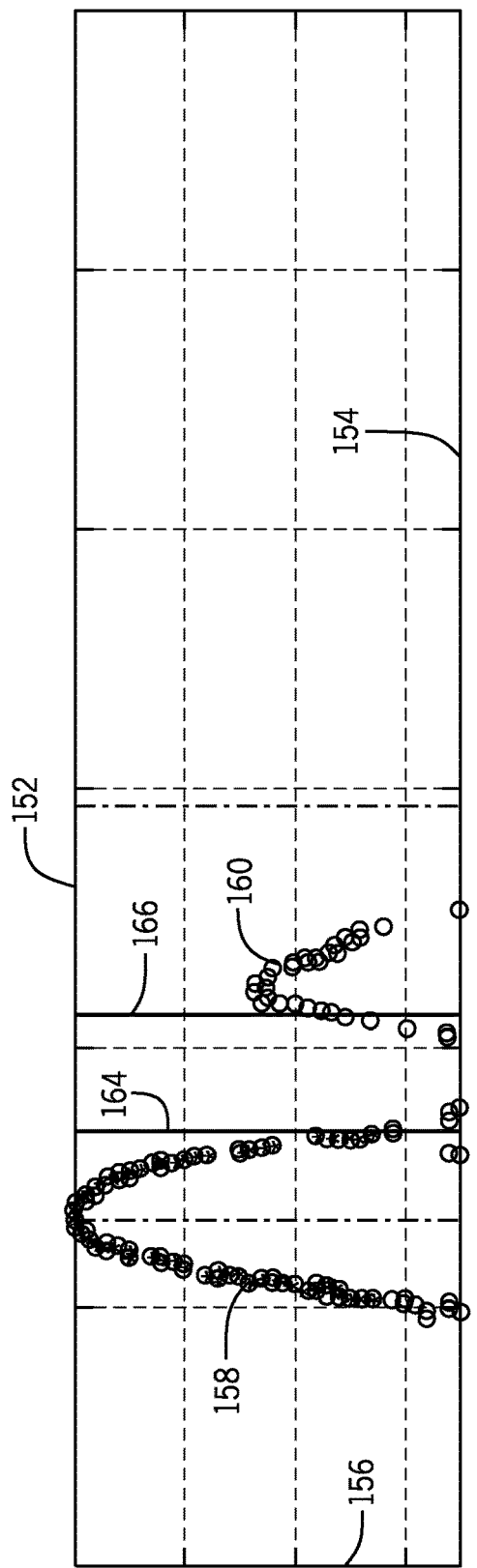
FIG. 6 is an embodiment of a sample screen from a graphical user interface showing an ultrasonic signal with a half-skip echo and a one-skip echo.

FIG. 6 shows a time of flight plot 152 of the raw data collected by the transducer 62. The x-axis 154 represents time of flight in microseconds (μs) and the y-axis 156 represents the signal amplitude in decibels (dB). The first arch-shaped distribution of dots 158 indicate a half-skip and the second arch-shaped distribution of dots 160 indicate a one-skip. Line 164 indicates the presence of a half-skip echo. Line 166 indicates the presence of a one-skip echo.

Figure 7:
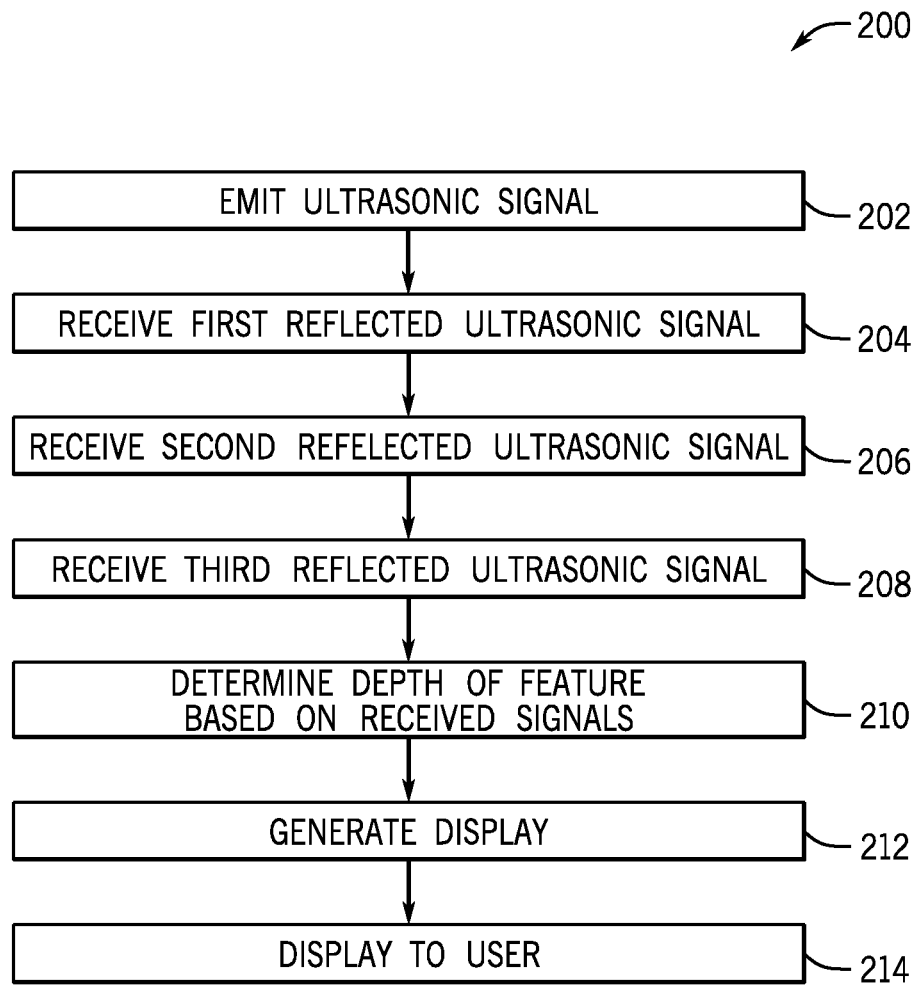
FIG. 7 is a flow chart of a process for analyzing ultrasonic pipeline inspection data.

FIG. 7 shows a process 200 for analyzing ultrasonic pipeline inspection data. In block 202, the process 200 emits an ultrasonic signal into a test specimen (e.g. pipeline wall 80). In block 204, the process may receive a first reflected ultrasonic signal from the pipeline wall 80 (e.g., half-skip echo). The first reflected ultrasonic signal is reflected from a feature 82 in the pipeline wall 80, and internally reflected within the pipeline wall once. In block 206, the process may receive a second reflected ultrasonic signal from the pipeline wall 80 (e.g., one-skip echo). The second reflected ultrasonic signal is reflected from a feature 82 in the pipeline wall 80, and internally reflected within the pipeline wall three times. In block 208, the process may receive a third reflected ultrasonic signal from the pipeline wall 80 (e.g., one-and-a-half-skip echo). The third reflected ultrasonic signal is reflected from a feature 82 in the pipeline wall 80, and internally reflected within the pipeline wall at five times. It should be understood, however, that the process 200 may not receive all three signals at a location of the transducer 62. Indeed, the threshold depth of the feature 82 may be determined based on as few as one of the three signals or any combination of the three signals at the location of the transducer.

In block 210, the threshold depth of the feature 82 is determined based on one or more of the received signals. For example, the threshold depth of the feature 82 may be determined based on the second signal, based on the first and second signals, based on the second and the third signals, or some combination thereof. Additionally, a determination of the feature thickness may consider the thickness of the pipeline wall 80, with width of the transducer 62, the incidence angle of emitted ultrasonic signal, the propagation angle of the ultrasonic signal through the pipeline wall 80, and so forth. Equations 1-6, which may be used to determine feature threshold depth, were discussed with regard to FIG. 5.

In block 212 the process 200 may generate a display summarizing the collected ultrasonic pipeline inspection data. In block 214 the generated display is transmitted and displayed to a user.

Technical effects of the invention include receiving multiple echoes of an ultrasonic signal emitted by a transducer inside of a pipeline in order to determine the presence of a feature (e.g., crack) as well as one or more characteristics (e.g., depth) of the detected feature. Because the disclosed techniques may be used on pipelines or other materials that may be buried underground, or otherwise difficult to access, knowledge of feature characteristics, rather than merely the presence of a feature, may help in understanding the severity of the feature or the condition of the material in general. This knowledge may help in determining the expected lifespan of the material and for making a decision as to when the material should be serviced or replaced.

This written description uses examples to describe the disclosed subject matter, including the best mode, and also to enable any person skilled in the art to practice the invention, including making and using any devices or systems and performing any incorporated methods. The patentable scope of the disclosed subject matter is defined by the claims, and may include other examples that occur to those skilled in the art.

The invention claimed is:
1. A method, comprising:
   emitting, via a transducer, an ultrasonic signal into a test specimen;
   receiving, via the transducer, one or more echoes from the test specimen, wherein the one or more echoes comprise reflections of the ultrasonic signal;

defining a half-skip coverage area, wherein the half-skip coverage area returns a half-skip echo of the one or more echoes when a feature extends into the half skip coverage area;

defining a one-skip coverage area, wherein the one-skip coverage area returns a one-skip echo of the one or more echoes when the feature extends into the one-skip coverage area;

defining a one-and-a-half skip coverage area, wherein the one-and-a-half-skip coverage area returns a one-and-a-half-skip echo of the one or more echoes when the feature extends into the one-and-a-half skip coverage area;

determining the feature extends into the half-skip coverage area of the test specimen when the half-skip echo is returned, wherein the half-skip echo is a first reflection of the ultrasonic signal reflected off the feature and internally reflected within the test specimen one time;

determining the feature extends into the one-skip coverage area of the test specimen when the one-skip echo is returned, wherein the one-skip echo is a second reflection of the ultrasonic signal reflected off the feature and internally reflected within the test specimen three times;

determining the feature extends into the one-and-a-half-skip coverage area of the test specimen when the one-and-a-half-skip echo is returned, wherein the one-and-a-half echo is a third reflection of the ultrasonic signal reflected off the feature and internally reflected within the test specimen five times; and determining a threshold depth of the feature in the test specimen based on determining the feature extends into the half-skip coverage area, the one-skip coverage area, the one-and-a-half-skip coverage area, or a combination thereof.

2. The method of claim 1, wherein the test specimen is a section of pipe.

3. The method of claim 2, wherein the feature is a notch or a crack extending from an exterior wall of the section of pipe.

4. The method of claim 2, wherein the feature is a notch or a crack extending from an interior wall of the section of pipe.

5. The method of claim 1, wherein the threshold depth is determined to be greater than a predetermined threshold based on determining the feature extends into the half-skip coverage area, the one-skip coverage area, the one-and-a-half-skip coverage area, or a combination thereof.

6. The method of claim 5, wherein the predetermined threshold is based on a thickness of the test specimen, a width of the transducer, an incidence angle of the emitted ultrasonic signal to the test specimen, and a propagation angle of the ultrasonic signal within the test specimen.

7. The method of claim 1, comprising:
applying a first set of parameters to determine the threshold depth of the feature in response to determining that the feature extends into the one-skip coverage area.

8. The method of claim 7, comprising:
applying a second set of parameters to determine the threshold depth of the feature in response to determining that the feature extends into the half-skip coverage area and the one-skip coverage area.

9. The method of claim 8, comprising
applying a third set of parameters to determine the threshold depth of the feature in response to determining that the feature extends into the one-skip coverage area and the one-and-a-half-skip coverage area.

10. The method of claim 1, wherein the threshold depth of the feature is determined irrespective of an amplitude of the first, the second, or the third reflected ultrasonic signal.

11. A non-transitory computer readable medium comprising executable instructions that when executed cause a processor to:

define a half-skip coverage area, wherein the half-skip coverage area returns a half-skip echo when a feature extends into the half skip coverage area;

define a one-skip coverage area, wherein the one-skip coverage area returns a one-skip echo when the feature extends into the one-skip coverage area;

define a one-and-a-half skip coverage area, wherein the one-and-a-half-skip coverage area returns a one-and-a-half-skip echo when the feature extends into the one-and-a-half skip coverage area;

determine a feature extends into the half-skip coverage area of a test specimen when the half-skip echo is returned, wherein the half-skip echo is a first reflection of an ultrasonic signal emitted into the test specimen, reflected off the feature, and internally reflected within the test specimen one time;

determine the feature extends into the one-skip coverage area of the test specimen when the one-skip echo is returned, wherein the one-skip echo is a second reflection of the ultrasonic signal reflected off the feature and internally reflected within the test specimen three times;

determine the feature extends into the one-and-a-half-skip coverage area of the test specimen when the one-and-a-half-skip echo is returned, wherein the one-and-a-half-skip echo is a third reflection of the ultrasonic signal reflected off the feature and internally reflected within the test specimen five times; and determine a threshold depth of the feature in the test specimen based upon determining the feature extends into the half-skip coverage area, the one-skip coverage area, the one-and-a-half-skip coverage area, or a combination thereof.

12. The non-transitory computer readable medium of claim 11, comprising executable instructions that when executed cause the processor to apply a first set of parameters to determine the threshold depth of the feature in response to determining that the feature extends into the one-skip coverage area.

13. The non-transitory computer readable medium of claim 12, comprising executable instructions that when executed cause the processor to apply a second set of parameters to determine the threshold depth of the feature in response to determining that the feature extends into the half-skip coverage area and the one-skip coverage area.

14. The non-transitory computer readable medium of claim 11, wherein the threshold depth is determined to be greater than a predetermined threshold based on determining the feature extends into the half-skip coverage area, the one-skip coverage area, the one-and-a-half-skip coverage area, or a combination thereof.

15. The non-transitory computer readable medium of claim 14, wherein the threshold depth of the feature is determined irrespective of an amplitude of the first, the second, or the third reflected ultrasonic signal.

16. The non-transitory computer readable medium of claim 13, comprising executable instructions that when executed cause the processor to apply a third set of parameters to determine the threshold depth of the feature in response to determining that the feature extends into the one-skip coverage area and the one-and-a-half-skip coverage area.

17. An ultrasonic pipeline inspection data analysis system comprising:
   a processor;
   communication circuitry; and
   a display;
   wherein the ultrasonic pipeline inspection data analysis system is configured to:
      define a half-skip coverage area, wherein the half-skip coverage area returns a half-skip echo when a feature extends into the half skip coverage area;
      define a one-skip coverage area, wherein the one-skip coverage area returns a one-skip echo when the feature extends into the one-skip coverage area;
      define a one-and-a-half skip coverage area, wherein the one-and-a-half-skip coverage area returns a one-and-a-half-skip echo when the feature extends into the one-and-a-half skip coverage area;
      receive one or more echoes from a test specimen, wherein the one or more echoes comprise reflections of an ultrasonic signal emitted into the test specimen;
      determine a feature extends into a the half-skip coverage area of the test specimen when the half-skip echo is returned, wherein the half-skip echo is a first reflection of the ultrasonic signal emitted into the test specimen, reflected off the feature, and internally reflected within the test specimen one time;
      determine the feature extends into a the one-skip coverage area of the test specimen when the one-skip echo is returned, wherein the one-skip echo is a second reflection of the ultrasonic signal reflected off the feature and internally reflected within the test specimen three times;
      determine the feature extends into a the one-and-a-half-skip coverage area of the test specimen when the one-and-a-half-skip echo is returned, wherein the one-and-a-half-skip echo is a third reflection of the ultrasonic signal reflected off the feature and internally reflected within the test specimen five times; and
      determine a threshold depth of the feature in the test specimen based upon determining the feature extends into the half-skip coverage area, the one-skip coverage area, the one-and-a-half-skip coverage area, or a combination thereof.

18. The ultrasonic pipeline inspection data analysis system of claim 17, wherein the ultrasonic pipeline inspection data analysis system is configured to apply a first set of parameters to determine the threshold depth of the feature in response to determining that the feature extends into the one-skip coverage area.

19. The ultrasonic pipeline inspection data analysis system of claim 18, wherein the ultrasonic pipeline inspection data analysis system is configured to apply a second set of parameters to determine the threshold depth of the feature in response to determining that the feature extends into the the half-skip coverage area and the the one-skip coverage area.

20. The ultrasonic pipeline inspection data analysis system of claim 19, wherein the ultrasonic pipeline inspection data analysis system is configured to apply a third set of parameters to determine the threshold depth of the feature in response to determining that the feature extends into the one-skip coverage area and the one-and-a-half-skip coverage area.

* * * * *